(12) United States Patent
Coste et al.

(10) Patent No.: US 7,351,818 B2
(45) Date of Patent: *Apr. 1, 2008

(54) METHOD TO IMPROVE TRANSLATION OF POLYPEPTIDES BY USING UNTRANSLATED REGIONS FROM HEAT-SHOCK PROTEINS

(75) Inventors: Herve Jean-Clement Coste, Les Ulis (FR); Jonathan Henry Ellis, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/167,614

(22) Filed: Jun. 27, 2005

(65) Prior Publication Data

US 2005/0266488 A1     Dec. 1, 2005

Related U.S. Application Data

(63) Continuation of application No. 09/936,506, filed as application No. PCT/EP00/02031 on Mar. 9, 2000, now Pat. No. 7,034,142.

(30) Foreign Application Priority Data

Mar. 11, 1999   (GB) ................................ 9905498.3

(51) Int. Cl.
    C07H 21/04     (2006.01)
(52) U.S. Cl. .................................... 536/24.1; 536/23.1
(58) Field of Classification Search ...................... None
    See application file for complete search history.

(56) References Cited

U.S. PATENT DOCUMENTS

| | | | |
|---|---|---|---|
| 5,371,015 A | 12/1994 | Sanford et al. | |
| 5,659,122 A | 8/1997 | Austin | |
| 5,697,901 A | 12/1997 | Eriksson | |

FOREIGN PATENT DOCUMENTS

| | | |
|---|---|---|
| WO | WO 87/00861 | 2/1987 |
| WO | WO 88/00239 | 1/1988 |
| WO | WO 94/11521 | 5/1994 |

OTHER PUBLICATIONS

Verma et al., Nature 389:239-242 (1997).*
Palu et al., J. Biotechnol. 68:1-13 (1999).*
Luo et al., Nature Biotechnol., 18:33-37 (2000).*
Fox, ASM New, 66(2):1-3 (2000).*
Fox, Yahoo! News, Jan. 14, 2003. Accessed Jan. 14, 2003 from http://new.yahoo.com/news?tmpl=story2&cid=570&u=/nm/20030114/sc_nm/health_genetherapy_dc&printer=1.*
Hunt et al., "Characterization and sequence of a mouse *hsp70* gene and its expression in mouse cell lines," Gene 87:199-204 (1990).
Illum et al., "Drug delivery," Current Opinion in Biotechnology 2:254-259 (1991).
Ingolia et al., "Sequence of three copies of the gene for the major Drosophila heat shock induced protein and their flanking regions," Cell 21:669-679 (Oct. 1980).
Joshi et al., "5' untranslated leader sequences of eukaryotic mRNAs encoding heat shock induced proteins", Nucleic Acids Research 23:4 541-549 (1995).
Kozac, "Structural features in eukaryotic mRNAs that modulate the initiation of translation," J. Biol. Chem. 266(30):19867-19870 (Oct. 1991).
Kozac, "An analysis of vertebrate mRNA sequences: intimations of translational control," J. Cell Biol. 115(4):887-903 (Nov. 1991).
Langer, "New methods of drug discovery," Science 249:1527-1533 (Sep. 1990).
Liarakos et al., "The translation efficiency of ovalbumin mRNA is determined in part by a 5'-end hairpin structure", Archives of Biochemistry and Biophysics 315:1 54-59 (1994).
Lindquist et al., "Selective translation and degradation of heat-shock messenger RNAs in Drosophila," Enzyme 44:147-166 (1990).
Luo et al., Nature Biotechnology 18:33-37 (2000).
McGarry et al., "The preferential translation of Drosophila hsp70 mRNA requires sequences in the untranslated leader," Cell 42:903-911 (Oct. 1985).
Mestril et al., "Isolation of a novel inducible rat heat-shock protein (HSP70) gene and its expression during ischaemia/hypoxia and heat shock," Biochem. J. 298(pt 3):561-569 (1994).
Morimoto et al., "Organization, nucleotide sequence, and transcription of the chicken HSP70 gene," J. Biol. Chem. 261:12692-12699 (1986).
Mosely et al., "Heat stress regulates the human 70-kDa heat-shock gene through the 3'-untranslated region", American Journal of Physiology 264:6 Part 1 L533-L537 (1993).
Myers et al., "Optimal alignments in linear space," CABIOS 4(1):11-17 (1988).
Palu et al., J. Biotechnol. 68:1-13 (1999).
Pitto et al., "Role of the leader sequence during thermal repression of translation in maize, tobacco, and carrot protoplasts", Plant Physiology (Rockville) 100:4 1827-1833 (1992).
Sachs et al., "Starting at the beginning, middle, and end: translation initiation in eukaryotes," Cell 89(6):831-838 (Jun. 1997).
Sainis et al., "The hsc70 gene which is slightly induced by heat is the main virus inducible member of the hsp70 gene family," FEBS Lett. 355(3):282-286 (Dec. 1994).

(Continued)

Primary Examiner—Nancy Vogel
(74) Attorney, Agent, or Firm—Michael M. Conger

(57) ABSTRACT

Untranslated regions associated with the heat shock response can be used to obtain increased efficiency of translation of polypeptides that are not necessarily normally associated with the heat shock response. This allows the development of greatly improved expression systems. The invention is also useful, for example, in the treatment of a patient suffering from a deficiency in the expression of a polypeptide and in the provision of vaccines.

1 Claim, 10 Drawing Sheets

OTHER PUBLICATIONS

Figure 1:
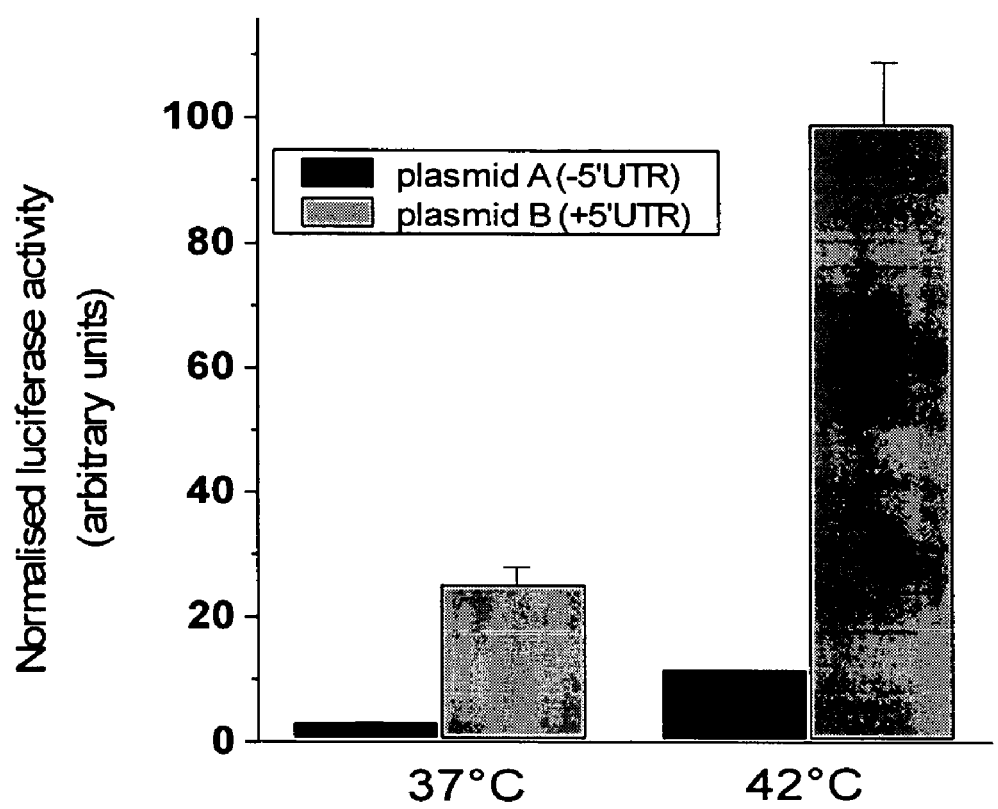

Schiller et al., "*Cis*-acting elements involved in the regulated expression of a human *HSP70* gene," *J. Miol. Biol.*, 203:97-105 (1988).

Stripecke et al., "Proteins binding to 5' untranslated region sites: a general mechanism for translational regulation of mRNAs in human and yeast cells," *Mol. Cell. Biol.* 14(9):5898-5909 (Sep. 1994).

Ting et al., "Human gene encoding the 78,000-Dalton glucose-regulated protein and its pseudogene: structure, conservation, and regulation," *DNA* 7(4):275-286 (1988). (GenBank: g183644).

Verme et al., "Gene therapy—promises, problems and prospects," *Nature* 389(6648):239-242 (Sep. 1997).

Zuker et al., "'Well-determined' regions in RNA secondary structure prediction: analysis of small subunit ribosomal RNA," *Nucleic Ac. Res.* 23(14):2791-2798 (1995).

Bonner et al., "The use of promoter fusions in Drosophila genetics: isolation of mutations affecting the heat shock response," *Cell* 37:979-991 (Jul. 1984).

Chiswell et al., "Phage antibodies: will new 'coliclonal' antibodies replace monoclonal antibodies?," *Tibtech* 10:80-84 (Mar. 1992).

DiNocera et al., "Transient expression of genes introduced into cultured cells of *Drosophila*,"*Proc. Natl. Acad. Sci. USA* 80:7095-7098 (Dec. 1983).

Fox, ASM News 66(2):1-3 (2000).

Fox Yahoo! News, Jan. 14, 2003. Accessed Jan. 14, 2003 from http://news.yahoo.com/news?tmpl=story2&cid=570&u=nm/20030114/sc_nm/health_genetherapy_dc&printer=1.

Geisow, "Improved selection systems for man-made antibodies," *Tibtech* 10:75-76 (Mar. 1992).

Gray et al., "Iron regulatory protein prevents binding of the 43S translation pre-initiation complex to ferritin and eALAS and mRNAs," *EMBO J.* 13(16):3882-3891 (1994).

Grosz et al., "Partial and complete sequences of Bovine HSP70-1 and HSP70-2 genes," Unpublished, Accession U02892, NID g414974, submitted Oct. 26, 1993.

Hess et al., "Sequence and structure determinants of Drosophila Hsp70 mRNA translation: 5'-UTR secondary structure specifically inhibits heat shock protein mRNA translation", *Nucleic Acids Research* 24:12 2441-2449 (1996).

Hultmark et al., "Translation and transcriptional control elements in the untranslated leader of the heat-shock gene *hsp22*," *Cell* 44:429-438 (Feb. 1986).

Hunt et al., "Conserved features of eukaryotic hsp-70 genes revealed by comparison with the nucleotide sequence of human hsp-70", *Proc. Natl. Acad. Sci. USA* 82:19 6455-6459 (1985).

Hunt et al., "Inducible expression of cDNAs in a vector based upon the mouse HSP70 heat-shock promoter", *J. Cell. Biochem.*, Suppl. 12D, 260 , XP000933846 abstract (1988).

Hunt et al., "Human heat shock protein (hsp 70) gene, complete cds", Accession M11717 (Jul. 1988).

* cited by examiner

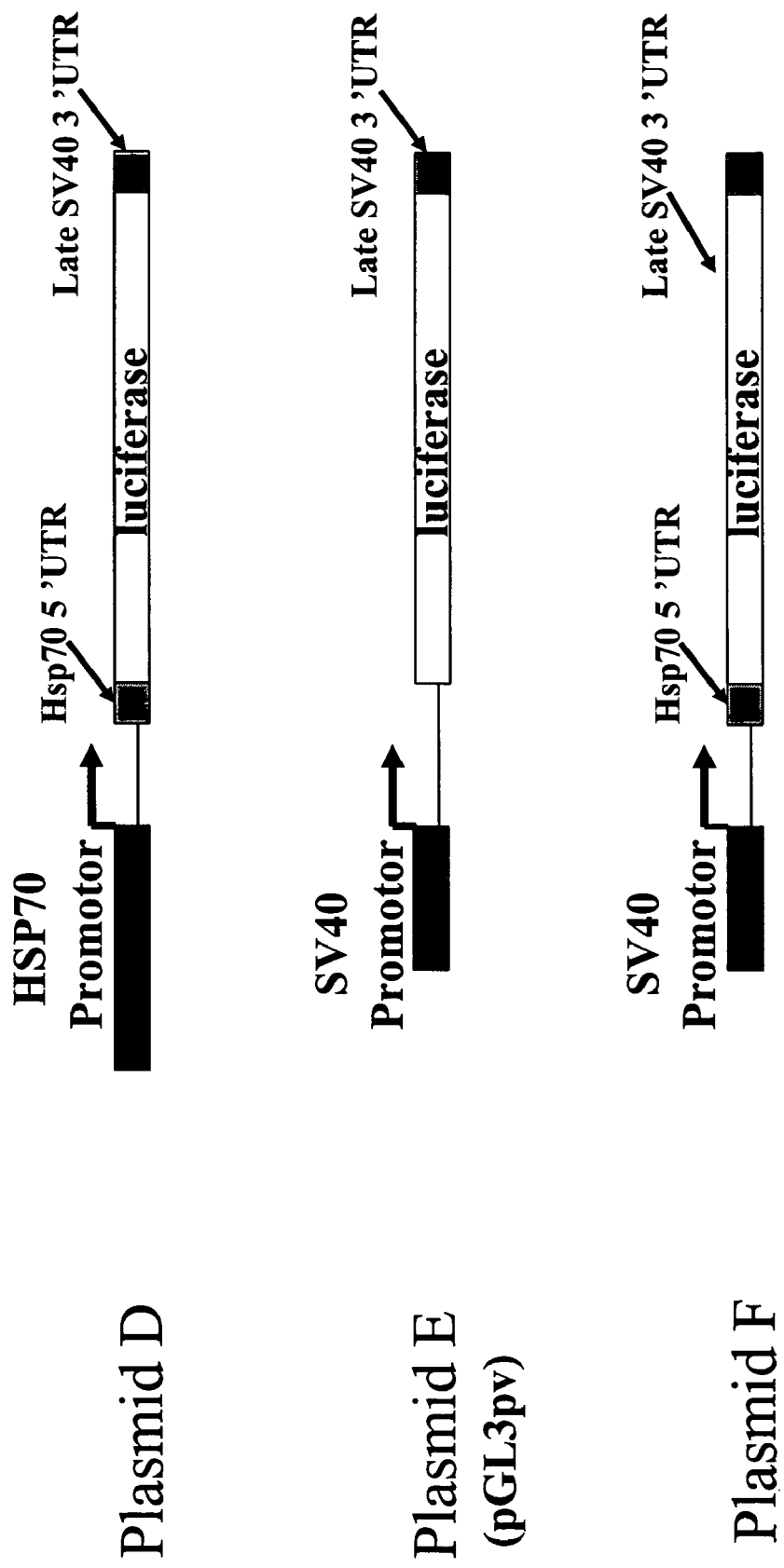

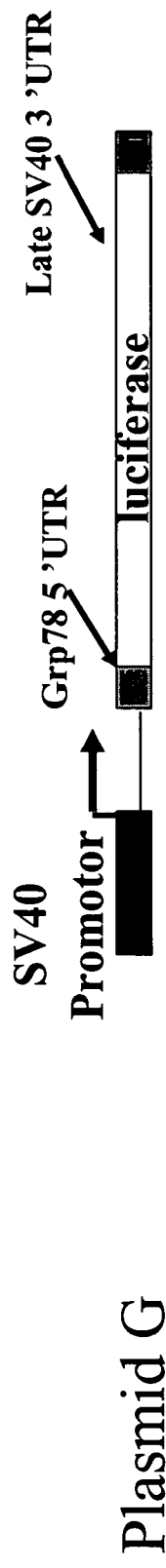
Plasmid G
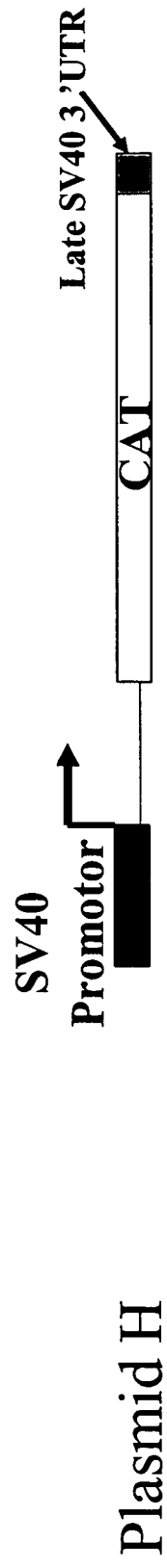
Plasmid H
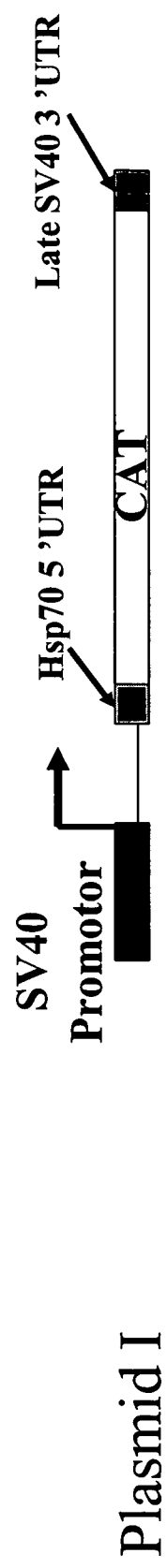
Plasmid I

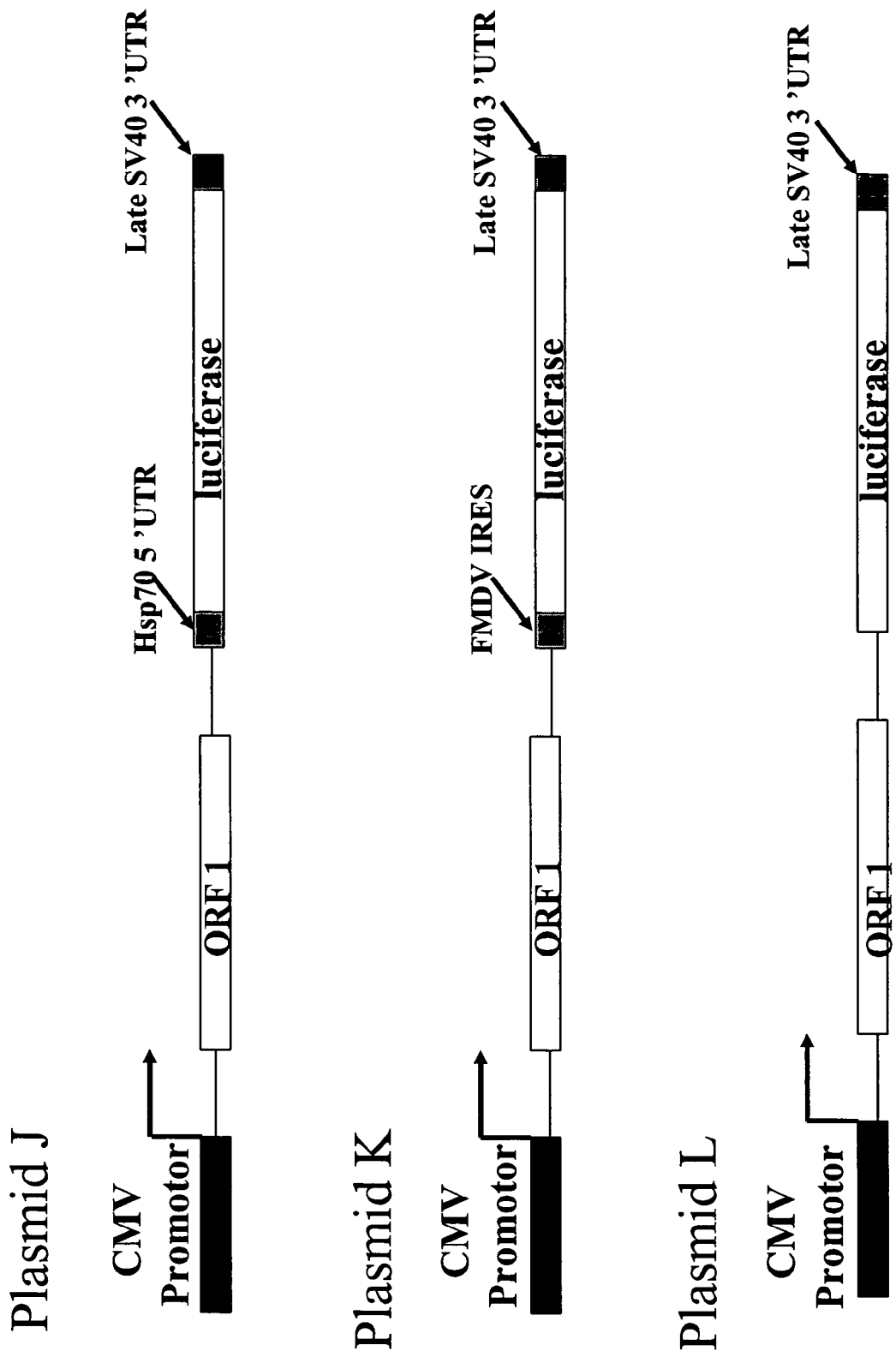

SEQUENCE LISTING

```
<160> NUMBER OF SEQ ID NOS: 9

<210> SEQ ID NO 1
<211> LENGTH: 215
<212> TYPE: DNA
<213> ORGANISM: Homo sapiens

<400> SEQUENCE: 1
ataacggcta gcctgaggag ctgctgcgac agtccactac cttttcgag agtgactccc      60 gttgtcccaa ggcttcccag agcgaacctg tgcggctgca ggcaccggcg cgtcgagttt    120
ccggcgtccg gaaggaccga gctcttctcg cggatccagt gttccgtttc cagcccccaa    180
tctcagagcc gagccgacag agagcaggga accgc                              215

<210> SEQ ID NO 2
<211> LENGTH: 215
<212> TYPE: RNA
<213> ORGANISM: Homo sapiens

<400> SEQUENCE: 2
auaacggcua gccugaggag cugcugcgac aguccacuac cuuuuucgag agugacuccc     60
guugucccaa ggcuucccag agcgaaccug ugcggcugca ggcaccggcg cgucgaguuu   120
ccggcguccg gaaggaccga gcucuucucg cggauccagu guuccguuuc cagcccccaa   180
ucucagagcc gagccgacag agagcaggga accgc                             215

<210> SEQ ID NO 3
<211> LENGTH: 119
<212> TYPE: DNA
<213> ORGANISM: Homo sapiens

<400> SEQUENCE: 3
agcagatccg gccgggctgg cggcagagaa accgcaggga gagcctcact gctgagcgcc     60
cctcgacgcg ggcggcagca gcctccgtgg cctccagcat ccgacaagaa gcttcagcc    119
```

<210> SEQ ID NO 4
<211> LENGTH: 217
<212> TYPE: DNA
<213> ORGANISM: Rattus sp.

<400> SEQUENCE: 4

```
ctcctcctaa tctgacagaa ccagtttctg gttccactcg cagagaagca gagaagcaga      60
gcaagcggcg cgttccgaac ctcgggcaag accagcctct cccagagcat ccccacgcga     120
agcgcaccct tctccagagc ataccccagc ggagcgcacc cttccccaga gcatccccgc     180
cgccaagcgc aaccttccag aagcagaccg cagcgac                              217
```

<210> SEQ ID NO 5
<211> LENGTH: 111
<212> TYPE: DNA
<213> ORGANISM: Gallus domesticus

<400> SEQUENCE: 5

```
cggcagatcg cgccgcagac agcagcgaga agcgggcgga ggagacgtga ctgcgagcga      60
gcaagtgact ggcggagcga gtggctgact gaccaagagg aatctatcat c              111
```

<210> SEQ ID NO 6
<211> LENGTH: 218
<212> TYPE: DNA
<213> ORGANISM: Mus sp.

<400> SEQUENCE: 6

```
aagctactca gaatcaaatc tggttccatc cagagacaag cgaagacaag agaagcagag      60
cgagcggcgc gttcccgatc ctcggccagg accagccttc cccagagcat ccacgccgcg     120
gagcgcaacc ttcccaggag catccctgcc gcggagcgca actttccccg gagcatccac     180
gccgcggagc gcagccttcc agaagcagag cgcggcgc                             218
```

<210> SEQ ID NO 7
<211> LENGTH: 180
<212> TYPE: DNA
<213> ORGANISM: Cercopithecus aethiops

<400> SEQUENCE: 7

```
gaattccgtt tctagagcgt ggctcccgtt gtcccgaggc ttcccagagc gaacctgtgc      60
ggctgcaggc accagcgccg ttgagtttcc ggcgttccgg aggactgagc tcttgtcacg     120
ggtcccgtcc gccgtttcca gtcccgaatc tcggagcgga cgagacagca gggcaccggc     180
```

<210> SEQ ID NO 8
<211> LENGTH: 214
<212> TYPE: DNA
<213> ORGANISM: Bos taurus

<400> SEQUENCE: 8

```
gccgcctgag gagaaacagc agcctggaga gagctgataa aacttacggc ttagtccgtg      60
agagcagttc cgcagacccg ctatctccaa ggaccgcgag gggcaccaga gcgttcagtt     120
ttcgggttcc gaaaagcccg agcttctcgt cgcagatcct cttcaccgat ttcagtttga     180
agcttatttc ggagccgaaa agcagggca ccgc                                  214
```

<210> SEQ ID NO 9
<211> LENGTH: 214
<212> TYPE: DNA
<213> ORGANISM: Homo sapiens

```
<400> SEQUENCE: 9
ataacggcta gcctgaggag ctgctgcgac agtccactac cttttcgag agtgactccc        60 gttgtcccaa ggcttcccag agcgaacctg tgcggctgca ggcaccggcg cgtcgagttt      120
ccggcgtccg gaaggaccga gctcttctcg cggatccagt gttccgtttc cagcccccaa      180
tctcagagcc gagccgaaga gagcagggaa ccgc                                  214
```

METHOD TO IMPROVE TRANSLATION OF POLYPEPTIDES BY USING UNTRANSLATED REGIONS FROM HEAT-SHOCK PROTEINS

CROSS-REFERENCE TO RELATED APPLICATIONS

This is a continuation of application Ser. No. 09/936,506, filed Dec. 20, 2001 now U.S. Pat. No. 7,034,142, which was filed pursuant to 35 USC 371 as a United States National Phase Application of International Patent Application Ser. No. PCT/EP00/02031 filed on 09 Mar. 2000, which claims priority from GB9905498.3 filed on 11 Mar. 1999 in the United Kingdom.

The present invention relates inter alia to the provision of increased polypeptide expression.

The human Hsp70A gene has been sequenced by Hunt C. and Morimoto R. I. (1985) *Proc. Natl. Acad. Sci. USA* 82, 6455-6459.) This gene encodes an mRNA containing a 5'-untranslated region (5'UTR) of 215 bases. As for most of the vertebrate Hsp mRNAs, the base composition of the human Hsp70 5'UTR is rich in guanosine and cytosine (~62%) (Joshi C. P. and Nguyen H. T. (1995) *Nucleic Acids Res.* 23, 541-549) suggesting that the human Hsp70 5'UTR has a high potential to form secondary stuctures in this region. It is believed that the function of the human Hsp70 5'UTR has never been previously studied.

In contrast, the *Drosophila* Hsp70 5'UTR has been extensively studied (Di Nocera P. P. and Dawid I. (1983) *Proc. Natl. Acad. Sci. USA* 80, 7095-7098; Bonner J. J. et al. (1984) *Cell* 37, 979-991; McGarry T. J. and Lindquist S. (1985) *Cell* 42, 903-911; Hultmark D. et al. (1986) *Cell* 44, 429438; Lindquist S. and Petersen R. (1990) *Enzyme* 44, 147-166). The sequence of the *Drosophila* Hsp70 5'UTR (Ingolia T. D. et al (1980) *Cell* 21, 669-679) has no significant homology with the human Hsp70 5'UTR. The lack of secondary structure in the *Drosophila* 5'UTR region due to a rich adenosine composition (~50%) allows efficient translation of this mRNA during heat shock (Hess M. A and Duncan R. F. (1996) *Nucleic Acids Res.* 12, 2441-2449).

Experimental studies with both in vivo and in vitro systems clearly demonstrate that mRNA with a high potential to form stable secondary structures in the 5'UTR tends to be inefficiently translated (Kozac M. (1991) *J. Biol. Chem.* 266, 19867-19870; Kozac M. (1991) *J. Cell Biol.* 115, 887-903). Moreover, structural motifs in the 5'UTR can provide sites for the binding of proteins which can act as negative regulators of translation (Gray N. K. and Hentze M. W. (1994) *EMBO J.* 13, 3882-3891; Stripecke R. et al (1994) *Mol. Cell. Biol.* 14, 5898-5909).

WO94/11521 is directed to providing inducible expression by using a bovine hsp70 promoter. The promoter may be associated with a human or bovine hsp70 5' untranslated region.

Surprisingly the present inventors have now identified a molecule with a high potential to form secondary structures that can provide increased efficiency of translation.

According to the present invention there is provided a DNA molecule that can be transcribed to provide an RNA molecule having an untranslated region that can provide an increased efficiency of translation of a polypeptide (relative to that obtainable when said untranslated region is absent) when operably linked to a coding region encoding said polypeptide; wherein said DNA molecule does not encode a mammalian hsp70.

Preferably the increased efficiency of translation is an increase of at least 10%. More preferably it is an increase of at least 100%. Most preferably it is an increase of at least 500%.

The use of the present invention to provide significantly increased efficiency of translation (and thereby to provide increased expression) contrasts with the invention disclosed in WO94/11521, for example. This discloses the possibility of using a human hsp70 5' untranslated region, but not for obtaining an increased efficiency of translation. In any event, as indicated above, WO94/11521 is specifically directed to the bovine hsp70 promoter and its use in promoting inducible expression. It is preferred that the bovine promoter hsp70 described in WO94/11521 is not used in the present invention. The human hsp70 promoter may for example be used in the present invention. Promoters which are not hsp promoters may also be used and are often preferred. Further, and in contrast to WO94/11521, heat shock is not required to increase the protein expression in the preswnt invention.

The untranslated region of the present invention is preferably located upstream of the coding sequence of the RNA molecule—i.e. it is a 5' untranslated region (a 5'UTR).

Preferred DNA molecules of the present invention comprise:

a) the sequence:

```
5'-ataacggctagcctgaggagctgctgcgacagtccactaccttttc
gagagtgactcccgttgtcccaaggcttcccagagcgaacctgtgcggct
gcaggcaccggcgcgtcgagtttccggcgtccggaaggaccgagctcttc
tcgcggatccagtgttccgtttccagcccccaatctcagagccgagccga
cagagagcagggaaccgc-3', SEQ ID NO: 1
```

[On transcription this sequence will produce an mRNA molecule having the following 5'UTR:

```
5'-auaacggcuagccugaggagcugcugcgacaguccactaccuuuuuc
gagagugacucccguugucccaaggcuucccagagcgaaccugugcggcu
gcaggcaccggcgcgucgaguuuccggcguccggaaggaccgagcucuuc
ucgcggauccaguguuccguuuccagcccccaaucucagagccgagccga
cagagagcagg gaaccgc-3'] SEQ ID NO: 2
``` b) the complement of the sequence given in a); or c) a sequence having substantial sequence identity with a sequence as defined in a) or b) above.

Thus a DNA molecule having a specific sequence that can be transcribed to provide the untranslated region of the present invention is within the scope of the present invention (see a) above).

The complement of this sequence is also within the scope of the present invention (see b) above) since the DNA molecule will normally be double-stranded. In any event the complement is useful in designing probes or primers or in providing antisense molecules (which can be used to reduce expression if expression levels become too high). Furthermore, cDNA (which is also within the scope of the present invention) will comprise the complement.

DNA molecules having substantial sequence identity with molecules described in a) and b) above may be used in a similar manner to said molecules and are therefore also within the scope of the present invention (see c) above).

The present invention further provides a DNA molecule as defined herein for use in therapy, particularly for use in therapeutic or prophylactic vaccination, preferably when administered by particle bombardment and most preferably for use in achieving an increased immune response. An increased immune response would be an immune response which is greater than that achieved with an equivalent construct which incorporates a promoter of the art, for example CMV immediate early promoter or SV40 promoter.

The UTR of the present invention is preferably capable of providing heat-shock responsiveness to the expression of a coding sequence in a given expression system. However this is not essential since the untranslated region can provide increased expression even in the absence of a heat shock response.

Desirably the untranslated region of the present invention has a G+C content of greater than 50%. More desirably this is greater than 55% or greater than 60%. High G+C contents are often associated with an increased tendency to form stable secondary structures.

Preferred DNA molecules of the present invention are those that can be transcribed to provide an RNA molecule having an untranslated region that can provide an increased efficiency of translation of a polypeptide (relative to that obtainable when said untranslated region is absent) when operably linked to a coding region encoding said polypeptide; wherein said DNA molecule does not encode human hsp70 and wherein said untranslated region has a $\Delta G$ of below $-10$ kCal/mol.

For the purposes of the present invention $\Delta G$ can be calculated using the RNA structural prediction program MFOLD (Zuker M. and Jacobson A. B. (1995) Nucleic Ac. Res. (23) 2791-2798). Predicted $\Delta G$ values may be calculated using the program located at the internet: http://mfold1.wustl.edu/~ mfold/mRNA/form1.cgi Preferably $\Delta G$ is below $-30$ kCal/mol or below $-40$ kCal/mol. More preferably $\Delta G$ is below $-50$ kCal/mol. Generally speaking, the lower the $\Delta G$ value, the greater the degree of secondary structure likely for a given polynucleotide region.

Increased translation efficiency can be achieved with the present invention in a wide variety of different systems. Indeed the present inventors have provided a 5'UTR upstream of the coding sequence of two very different reporters (firefly luciferase and chloramphenicol-acetyl-transferase) and have demonstrated significantly increased expression of the reporter (5- to 10-fold) in normal transfected cell culture conditions.

This effect has been obtained in two different promoter contexts (HSP- and SV40-promoter) and in various human cell lines (HepG2,Hep3B,HEK293,WI-38). The 5'UTR did not not modify the level of mRNA but increased the efficiency of translation. This pure translational effect and the fact that the heat shock response is a highly conserved mechanism provide evidence in support of the broad applicability of the present invention.

In principle the expression of any given polypeptide can be increased using the present invention. However it is preferred to use the present inventions to increase the expression of polypeptides that are not heat shock proteins. Most preferably the present invention is used in providing increased expression of polypeptides of relatively high commercial or scientific value. It can for example be used to increase the expression of therapeutic polypeptides. These include interferons, hormones (e.g. insulin), interleukins, erythropoietin, tpa, growth factors, etc. The present invention can of course also be used to increase the expression of other polypeptides—e.g. polypeptides useful in the agro-alimentary or cosmetic industries A further aspect of the present invention is the provision of new vectors. These may be derived by modifying known vectors to include a DNA sequence which, on transcription, provides an untranslated sequence of the present invention. This can be done by recombinant DNA technology or by mutagenesis techniques. Alternatively vectors may be constructed de novo.

Vectors can be used for many purposes—e.g. for amplifying, maintaining or manipulating sequences of interest, for the production of desired gene products, for medicinal purposes etc. Vectors (and nucleic acids) of the present invention may be purified and provided in isolated form if desired. They may be provided in a form substantially free of contaminating proteins.

Many different types of vector can be provided, including plasmids, phasmids, cosmids, YACs, PACs and viruses. Viral vectors include bacteriophage vectors. These can be used to generate high titre combinatorial libraries. Using 'phage display many different polypeptides can be expressed (e.g. antibodies/parts thereof). These techniques are described for example by M J Geisow in *Tibtech* 10, 75-76 (1992) and by D. Chiswell et al in *Tibtech* 10, 8-84 (1992). Other vectors can be used in addition to those described above.

Whatever vectors are used, it is preferred that they include one or more selectable markers—e.g. drug resistance markers and/or markers enabling growth on a particular medium. In some cases a vector will include a marker that is inactivated when a nucleic acid molecule according to the present invention is inserted into the vector. Here there is desirably at least one further marker, which is different from the marker that is inactivated.

Preferred vectors of the present invention may be introduced into a cell that can then be used to express a desired polypeptide (although cell-free expression systems can also be used). For example, polypeptides can be produced by micro-organisms such as bacteria or yeast, by cultured insect cells (which may be baculovirus-infected), by mammalian cells (such as CHO cells) or by transgenic animals that, for instance, secrete the proteins in milk (see e.g. international patent application WO88/00239). Where glycosylation is desired, eukaryotic expression systems are preferred.

Particularly suitable expression systems are cell lines that can divide in culture and that can be maintained in culture over a long period. These are often referred to as immortal cell lines. Preferred cell lines are mammalian or human cell lines.

Various transcriptional and translational control sequences may be used in expression systems of the present invention. These can be operably linked to a coding sequence encoding a polypeptide to be expressed. The control sequences may be heterologous to the coding sequence. Promoter, operator and/or enhancer sequences may, for example, be provided, as may polyadenylation sites, splice sites, stop and start codons, etc. Polypeptides may initially be expressed to include signal sequences. Different signal sequences may be provided for different expression systems. Alternatively, signal sequences may be absent.

Techniques for manipulating nucleic acids, for expressing and purifying polypeptides, etc. are well known to a person skilled in the art of biotechnology. Such techniques are disclosed in standard text-books, such as in Sambrook et al [*Molecular Cloning* 2nd Edition, Cold Spring Harbor Laboratory Press (1989)]; in Old & Primrose [*Principles of Gene*

*Manipulation* 5th Edition, Blackwell Scientific Publications (1994)]; and in Stryer [*Biochemistry* 4th Edition, W H Freeman and Company (1995)].

The present invention is useful in medicine (both in human treatment and in veterinary treatment). It can be used to treat an existing condition or can be used for prophylactic treatment. In particular, the present invention is useful for treating a disorder involving a deficiency in the expression of a polypeptide. It will therefore be appreciated that the present invention can be used in gene therapy, especially for treating disorders arising due to mutations affecting the expression of a single polypeptide (although it is generally applicable and can also be used to treat disorders affecting the expression of a plurality of polypeptides). Gene therapy may be used, for example, in the treatment of cancer, cardiovascular disorders, cystic fibrosis, etc.

Treatment of a disorder involving a deficiency in the expression of a polypeptide can be performed by providing a patient with a DNA molecule of the present invention that encodes said polypeptide, with a vector comprising said DNA molecule, or with a cell comprising said DNA molecule or vector. Expression of the polypeptide within the patient can then be used to compensate for, or at least to reduce the deficiency. The DNA molecule or the vector can be allowed to integrate into a patient's genome.

Suitable techniques for introducing a nucleic acid molecule or vector into a patient include topical application of the 'naked' nucleic acid in an appropriate vehicle. The nucleic acid may be present together with a pharmaceutically acceptable excipient, such as phosphate buffered saline (PBS). One technique involves particle bombardment (which is also known as 'gene gun' technology and is described in U.S. Pat. No. 5,371,015). Here inert particles (such as gold beads coated with a nucleic acid) are accelerated at speeds sufficient to enable them to penetrate a surface of a recipient (e.g. skin) by means of discharge under high pressure from a projecting device. (Particles coated with a nucleic acid molecule of the present invention are within the scope of the present invention, as are devices loaded with such particles.) Other methods of administering the nucleic acid directly to a recipient include ultrasound, electrical stimulation, electroporation and microseeding. Particularly preferred is the microseeding mode of delivery. This is described in U.S. Pat. No. 5,697,901.

Nucleic acid molecules of the present invention may also be administered by means of specialised delivery vectors useful in gene therapy. Gene therapy approaches are discussed for example by Verme et al, Nature 1997, 389:239-242. Both viral and non-viral systems can be used. Viral based systems include retroviral, lentiviral, adenoviral, adeno-associated viral, herpes viral and vaccinia-viral based systems. Non-viral based systems include direct administration of nucleic acids and liposome-based systems.

A nucleic acid sequence of the present invention may even be administered by means of transformed cells. Such cells include cells harvested from a subject. The nucleic acid molecules of the present invention can be introduced into such cells in vitro and the transformed cells can later be returned to the subject. The nucleic acid molecules need not be introduced into the cells as vectors, since non-vector nucleic acid molecules can be introduced. Some such molecules may integrate into nucleic acid already present in a cell by homologous recombination events. A transformed cell may, if desired, be grown up in vitro and one or more of the resultant cells may be used in the present invention.

Cells can be provided at an appropriate site in a patient by known surgical or microsurgical techniques (e.g. grafting, micro-injection, etc.)

Another way of treating a deficiency in the expression of a polypeptide comprises providing a patient with a DNA molecule that can be transcribed to provide the untranslated region of the present invention. This molecule can be provided in a manner to allow it to become operably linked with a sequence already present in the patient that encodes said polypeptide.

A further way of treating a deficiency in the expression of a polypeptide comprises providing a patient with an RNA molecule coding for said polypeptide, which RNA molecule is pruducable by transcribing a DNA molecule of the present invention. The RNA molecule can then be translated in vivo to provide the polypeptide.

A still further way of treating a deficiency in the expression of a polypeptide, comprises providing a patient with the polypeptide, wherein the polypeptide has been produced using an expression system of the present invention.

The present invention is also useful in providing DNA vaccines. The direct injection of gene expression cassettes into a living host transforms a number of cells into factories for the production of the introduced gene products. Expression of these delivered genes has important immunological consequences and may result in the specific immune activation of the host against expressed antigens. Although vaccines produced by recombinant DNA technology are safer than traditional vaccines, which are based on attenuated or inactivated bacteria or viruses, they are often poorly immunogenic. Placing an untranslated region of the present invention upstream of the coding sequence of a gene to be delivered in a DNA vaccine can significantly increase expression and can therefore increase immunogenicity. Due to the highly conserved mechanism of heat shock response an increase in polypeptide expression can be expected in every tissue where the gene is delivered. DNA vaccines can be designed to prevent viral, bacterial and parasitic infections (e.g. diphtheria, malaria, leishmaniasis, toxoplasmosis, schistosomiasis, cryptosporidiosis, tuberculosis, HIV, HSV, influenza virus, hepatitis A, B and C), but can also be used for treating cancer, immune-related diseases or for contraceptive purposes. All of these applications are within the scope of the present invention.

When used in medicine, the nucleic acid molecules, vectors, polypeptides and cells discussed above will usually be in the form of a pharmaceutically acceptable composition. One or more pharmaceutically acceptable carriers may be present in such a composition. A pharmaceutical composition within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) routes. Different drug delivery systems can be used to administer pharmaceutical compositions, depending upon the desired route of administration. Drug delivery systems are described, for example, by Langer (*Science* 249, 1527-1533 (1991)) and by Illum and Davis (*Current Opinions in Biotechnology* 2, 254-259 (1991)). In summary, it will be appreciated that the present invention can be used to manufacture medicaments for use in the treatment of one or more of the disorders discussed herein.

In addition to the uses discussed above, the invention is of broad applicability for research purposes.

Cell transfection is a technique classically used in research to study the function of a polypeptide. Moreover, many cellular screenings are performed on cells transfected so as to express a given polypeptide. This technique is also used to study the function of a promoter using reporters (e.g. luciferase, chloramphenicol-acetyl-transferase, β-galactosidase etc.) Providing an untranslated region of the present invention upstream of the coding sequence of a reporter gene can significantly increase the expression of a polypeptide of interest. The sensitivity of such experiments can therefore be increased.

Increased polypeptide expression is also useful in many other research applications where large amounts of a given polypeptide need to be synthetized. For example it is useful in structural studies (crystallography, NMR, etc), for the production of antibodies or fragments thereof (which can be used for example in purification or in binding studies), or for high throughput screening.

The present invention is also useful for diagnostic purposes. For example, it can be used to increase the provision of antibodies or fragments thereof useful in diagnosing the presence of a moiety associated with a particular disorder. The present invention will now be described by way of example only with reference to the accompanying drawings, wherein:

FIG. 1 shows the effect of the human Hsp70 5'UTR on the expression of a luciferase reporter driven by the human HSP70 promoter. The human HSP70 promoter was cloned upstream of the coding sequence of the firefly luciferase gene in the absence or presence of the 5' UTR (plasmids A and B respectively). For both plasmids the 3'UTR was the HSP70 3'UTR. HepG2 cells were transfected with these two chimeric constructs and the levels of luciferase were compared either under normal conditions or after a 30 min heat-shock at 42° C.

Figure 2:
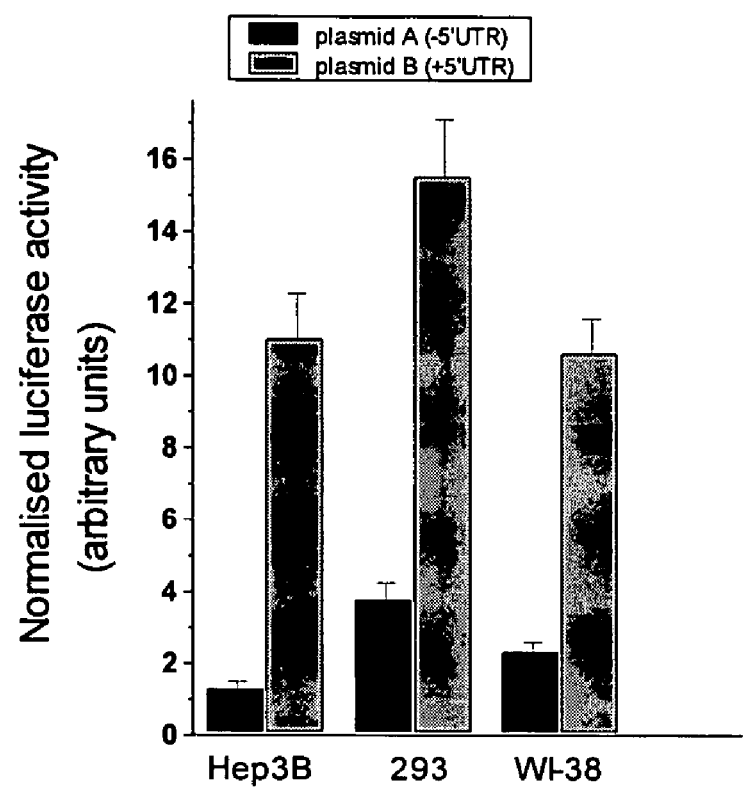

FIG. 2 shows the effect of the human Hsp70 5'UTR on the expression of luciferase in various cell lines. The same constructs (A and B) were transfected in three other human cell lines (Hep3B, HEK293, WI-38) and the luciferase levels were compared under normal cell culture conditions.

Figure 3:
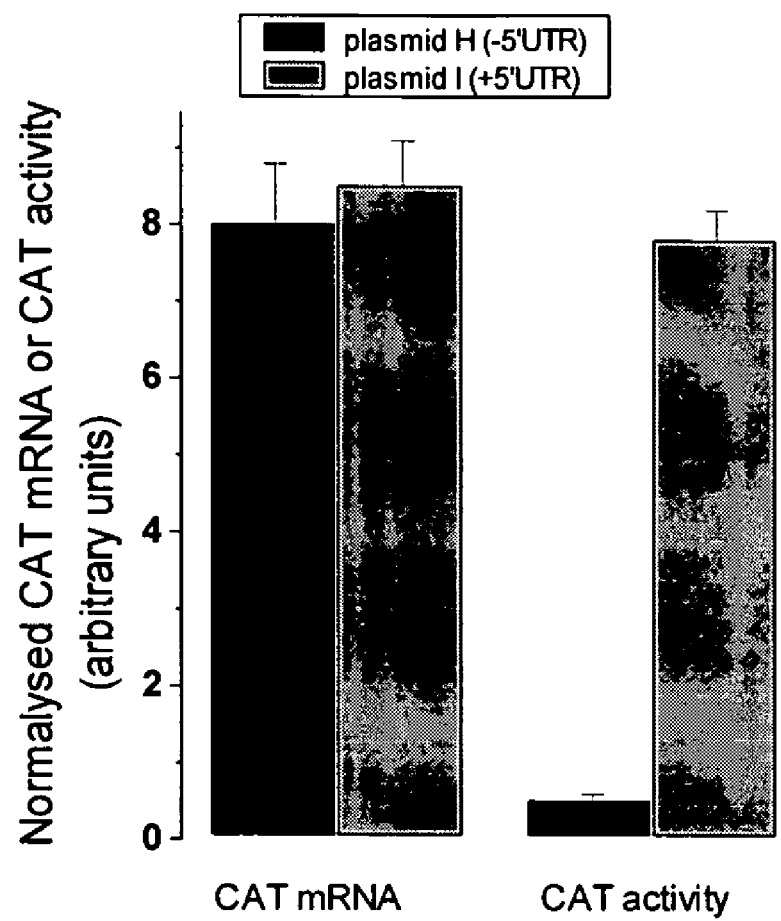

FIG. 3 shows the effect of the human Hsp70 5'UTR on the translational efficiency of the chloramphenicol-acetyl-transferase mRNA. The SV40 promoter was cloned upstream of the coding sequence of the chloramphenicol-acetyl-transferase (CAT) gene in the absence or presence of the human Hsp70 5' UTR (plasmids H and I respectively). HepG2 cells were transfected with these two constructs and the levels of CAT mRNA and activity were measured.

Figure 4:
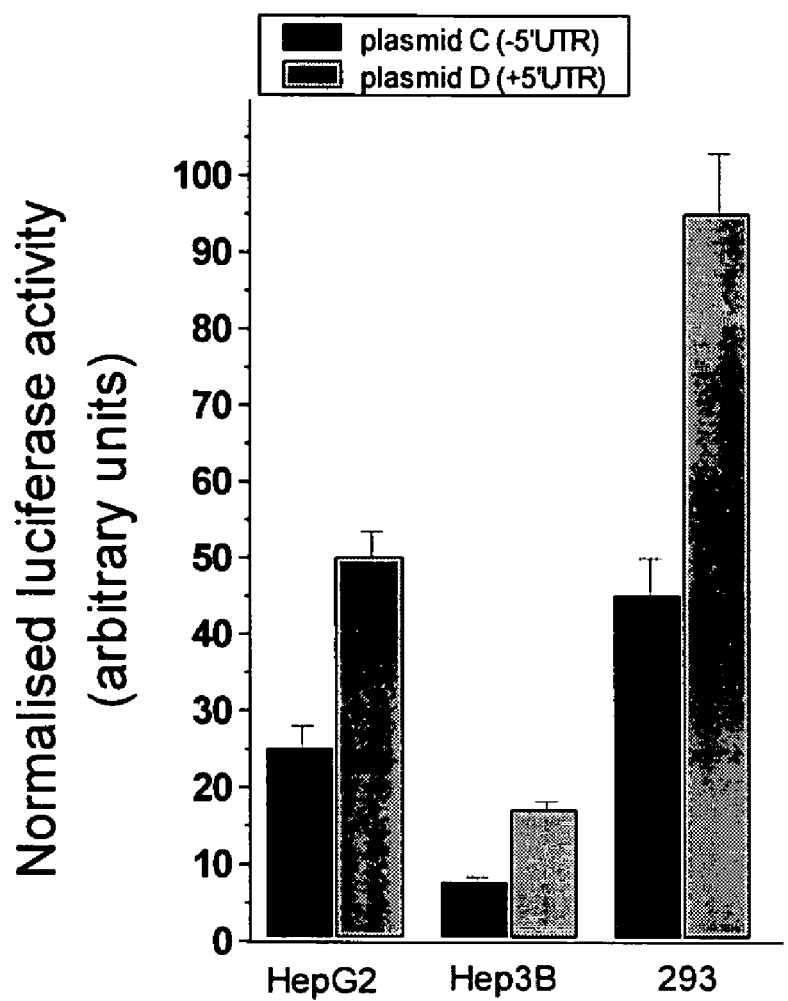

FIG. 4 shows the effect of the human Hsp70 5'UTR on the expression of luciferase in the presence of the SV40 3'UTR. The Hsp70 promoter was cloned upstream of the coding sequence of the luciferase in the absence or presence of the human Hsp70 5'UTR (plasmids C and D respectively), for both plasmids the 3'UTR was the SV40 3'UTR. The constructs (C and D) were transfected in three human cell lines (HepG2, HEK293, Hep3B) and the luciferase levels were compared under normal cell culture conditions.

Figure 5:
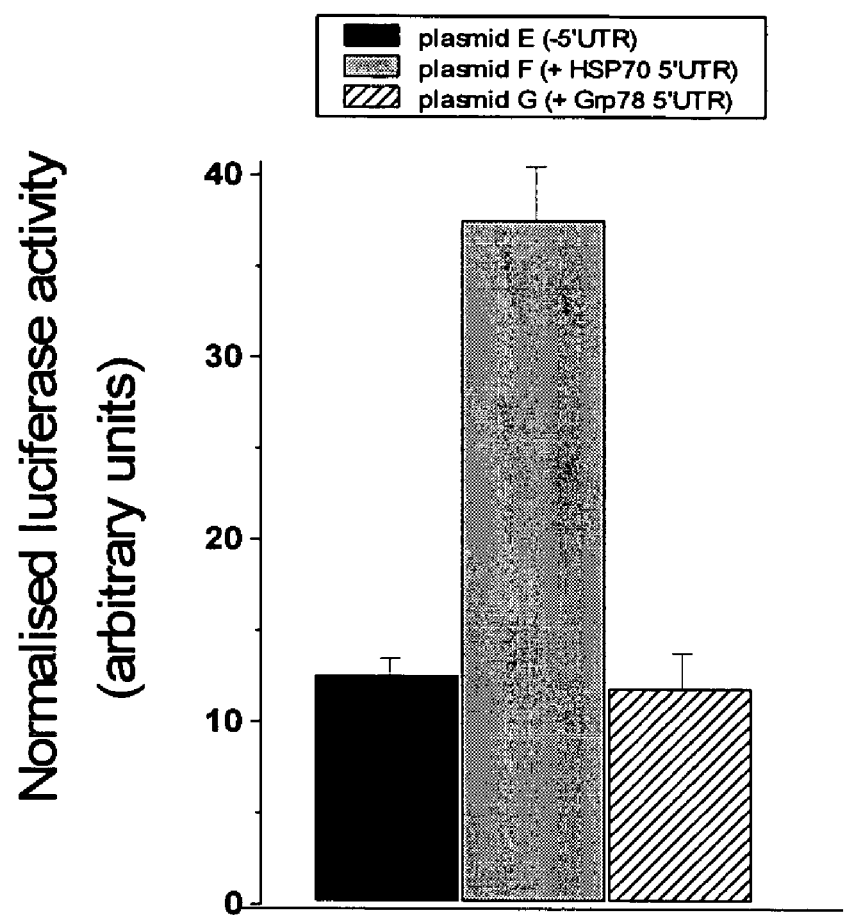

FIG. 5 shows a comparison of the effect of the human Hsp70 5'UTR with the human Grp78 5'UTR on the expression of the luciferase. The SV40 promoter was cloned upstream of the coding sequence of the luciferase in the presence of the human Hsp70 5'UTR (plasmid F) or of the human Grp78 5'UTR (plasmid G) or in the absence of any 5'UTR (plasmid E). HepG2 cells were transfected with these three constructs and the the luciferase levels were compared under normal cell culture conditions.

Figure 6:
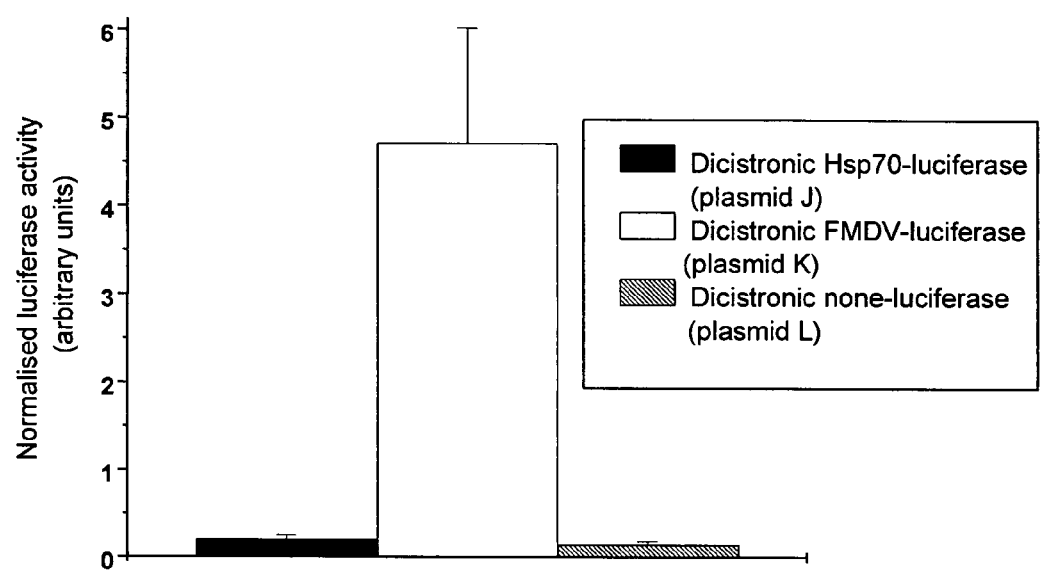

FIG. 6 shows a comparison of the effect of the FMDV IRES with the human Hsp70 5'UTR on the expression of luciferase in a dicistronic context. The CMV promoter and a first ORF were cloned upstream of the coding sequence of the luciferase in the presence of the human Hsp70 5'UTR (plasmid J) or of the FMDV IRES (plasmid K). HepG2 cells were transfected with these three constructs and the the luciferase levels were compared under normal cell culture conditions.

Figure 7:
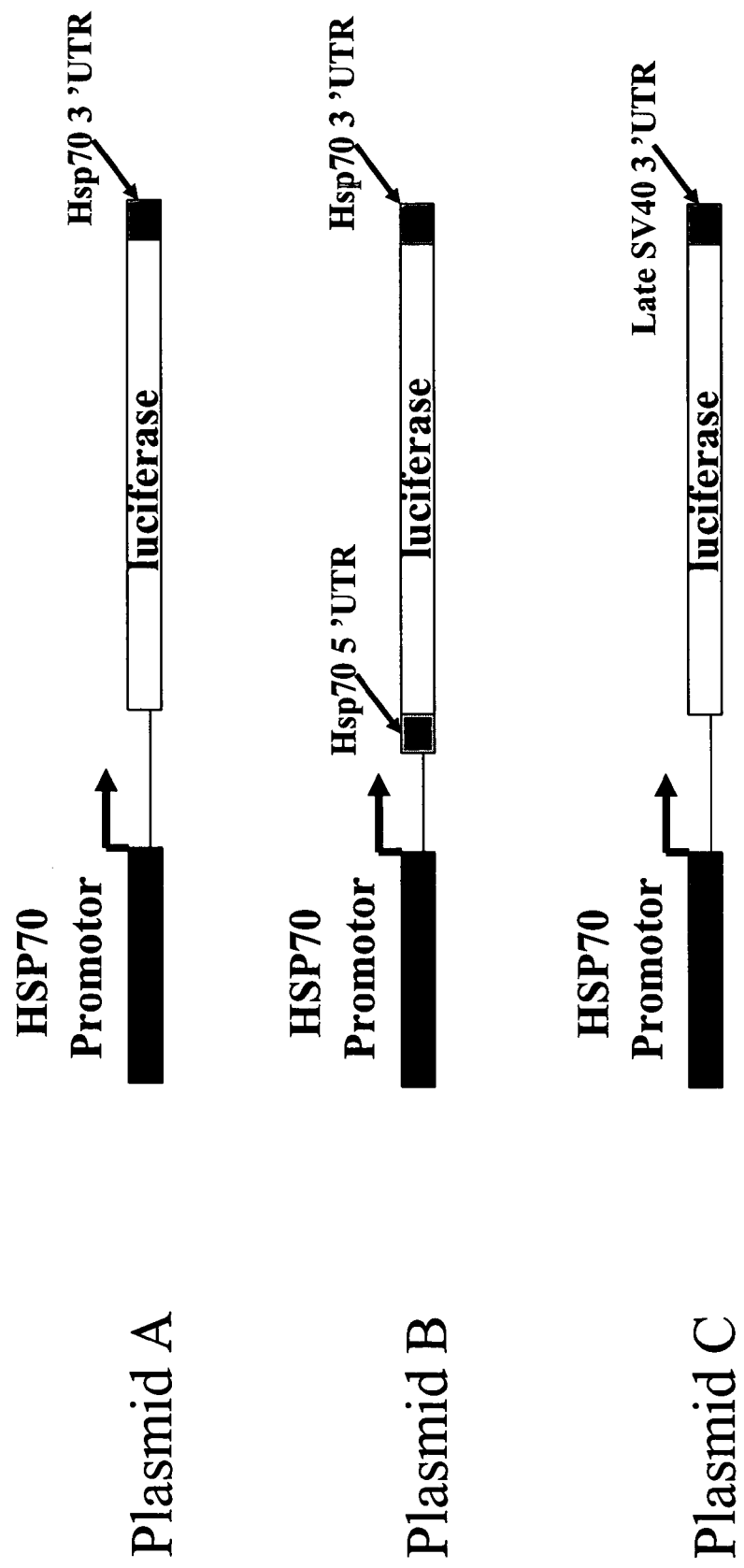

FIG. 7 is a schematic map of plasmids A to L referred to in the specification.

The following sequences are provided for reference purposes and show the hsp70 5'UTR sequences from various species:

```
Human HSP70A
Hunt C. and Morimoto R. I. (1985)
Proc. Natl. Acad. Sci. USA 82, 6455 6459 ataacggctagcctgaggagctgctgcgacagtccactacctttttcgag
agtgactcccgttgtcccaaggcttcccagagcgaacctgtgcggctgca
ggcaccggcgcgtcgagtttccggcgtccggaaggaccgagctcttctcg
cggat ccagtgttccgtttccagcccccaatctcagagccgagccgaca
gagagcagggaaccgc SEQ ID NO: 1

Human HSP70B
Schiller et al (1988) J. Miol. Biol. 203, 97 105 agcagatccggccgggctggcggcagagaaaccgcagggagagcctcact
gctgagcgcccctcgacgcgggc ggcagcagcctccgtggcctccagca
tccgacaagaagcttcagcc SEQ ID NO: 3

Rat HSP70
Mestril, R., Chi, S. H., Sayen, M. R. and
Dillmann, W. H. Biochem. J. 298 Pt 3,
561 569 (1994)

ctcctcctaatctgacagaaccagtttctggttccactcgcagagaagca
gagaagcagagcaagcggcgcgttccgaacctcgggcaagaccagcctct
cccagagcatcccacgcgaagcgcacccttctccagagcatacccagc
ggagcgcacccttcccagagcatccccgccgccaagcgcaaccttccag
aagcagaccgcagcgac SEQ ID NO 4

Chicken HSP70
Morimoto, R. I., Hunt, C., Huang, S. -Y.,
Berg, K. L. and Banerji, S. S. J. Biol. Chem. 261,
12692 12699 (1986)

cggcagatcgcgccgcagacagcagcgagaagcgggcggaggagacgtga
ctgcgagcgagcaagtgactg gcggagcgagtggctgactgaccaagag
gaatctatcatc SEQ ID NO: 5

Mouse HSP70
Hunt, C. and Calderwood, S. B.
Gene 87, 199-204 (1990)

aagctactcagaatcaaatctggttccatccagagacaagcgaagacaag
agaagcagagcgagcggcgcgttcccgatcctcggccaggaccagccttc
cccagagcatccacgccgcgggagcgcaaccttcccaggagcatccctgcc
gcggagcgcaactttccccggagcatccacgccgcgggagcgcagccttcc
agaagcagagcgcggcgc SEQ ID NO: 6

African Green monkey HSP70
Sainis, I., Angelidis, C., Pagoulatos, G. and
Lazaridis, I. FEBS Lett. 355 (3), 282 286 (1994)

gaattccgtttctagagcgtggctcccgttgtcccgaggcttcccagagc
gaacctgtgcggctgcaggcaccagcg ccgttgagtttccggcgttccg
gaggactgagctcttgtcacgggtcccgtccgccgfttccagtcccgaat
ctcggagc ggacgagacagcagggcaccggc SEQ ID NO: 7

Bos taurus Angus HSP70
ACCESSION U02892
NID g414974
AUTHORS Grosz, M. D. and Skow, L. C.(unpublished)

gccgcctgaggagaaacagcagcctggagagagctgataaaacttacggc
```

-continued
ttagtccgtgagagcagttccgcagacccgctatctccaaggaccgcgag
gggcaccagagcgttcagftftcgggttccgaaaagcccgagcftctcgt
cg cagatcctcttcaccgatttcagtttgaagcttattcggagccgaaa
aagcagggcaccgc SEQ ID NO: 8

This sequence is only available in Genbank data base (g414974).

Below, for reference purposes, are shown the sequence identity of the human hsp70A 5'UTR with the hsp70 5'UTR from various other species and with the human HSP70B 5'UTR:

--- var/tmpweb/analseq/al9179/s1: 215 nt
ALIGN calculates a global alignment of two sequences
version 2.0uPlease cite: Myers and Miller, CABIOS (1989) 4: 11-17
      human        215 nt vs.
      rat           217 nt
scoring matrix: DNA, gap penalties: −16/−4
      49.2% identity;      Global alignment score: −102
resetting matrix to DNA
/var/tmpweb/analseq/al10142/s1: 215 nt
ALIGN calculates a global alignment of two sequences
version 2.0uPlease cite: Myers and Miller, CABIOS (1989) 4: 11-17
      human        215 nt vs.
      chicken      111 nt
scoring matrix: DNA, gap penalties: −16/4
      32.7% identity;      Global alignment score: −349
resetting matrix to DNA
/var/tmpweb/analseq/al10710/s1: 215 nt
ALIGN calculates a global alignment of two sequences
version 2.0uPlease cite: Myers and Miller, CABIOS (1989) 4: 11-17
      human        215 nt vs.
      mouse        218 nt
scoring matrix: DNA, gap penalties: −16/−4
      49.6% identity;      Global alignment score: −39
resetting matrix to DNA
/var/tmpweb/analseq/al10998/s1: 215 nt
ALIGN calculates a global alignment of two sequences
version 2.0uPlease cite: Myers and Miller, CABIOS (1989) 4: 11-17
      human        215 nt vs.
      green monkey  180 nt
scoring matrix: DNA, gap penalties: −16/−4
      69.3% identity;      Global alignment score: 403

---

EXAMPLES

Materials

Cell culture medium (BME and MEM), penicillin, streptomycin, trypsin-EDTA solution, versene, non-essential amino acids and restriction enzymes were obtained from Gibco, Life Technologies, Inc. Foetal bovine serum (heat inactivated) was from HyClone, Culture flasks (TPP T150) and 60 mm culture dishes (Falcon) were purchased from Becton Dickson. Plasmids were obtained from Promega. The HepG2, Hep3B, HEK293 and WI-38 cell lines were obtained from the American Type Culture Collection.

Methods

Plasmids Constructs

HSP70 reporter vectors were generated using pGL3 promoter vector plasmid for the firefly luciferase assay, or pCAT3 promoter vector plasmid for the chloramphenicol acetyl transferase (CAT) assay were purchased from PROMEGA. Human HSP70 promoter, human HSP70 5'UTR and 3'UTR were PCR-amplified (Advantage GC genomic PCR kit, Clontech) from a human genomic bank (Clontech). Oligonucleotides were designed from the human hsp70A gene (Hunt C. and Morimoto R. I. (1985) Proc. Natl. Acad. Sci. USA 82, 6455-6459) (GenBank: g184416).

Sequence of the human Hsp70 5'UTR and regions (bold characters) utilized to design oligonucleotides for the PCR reaction:

5'-ataacggctagcctgaggagctgctgcgacagtccactaccttttc gagagtgactcccgttgtcccaaggcttcccagagcgaacctgtgcggct gcaggcaccggcgcgtcgagtttccggcgtccggaaggaccgagctcttc tcgcgg atccagtgttccgtttccagcccccaatctcagagccgagccg a agagagcagggaaccgc-3' SEQ ID NO: 9

For the the human Grp78 5'UTR primers were designed using the sequence published by Ting J. and Lee A. S. (1988) DNA (4) 275-278 (GenBank: g183644).

The 5'UTRs were inserted between the Hind III and Nco I sites, HSP70 promoter between Bgl II and Nco I sites. The human Hsp70 3'UTR was inserted between the Xbal and BamH1 sites.

Dicistronic constructs were generated using pCI-neo (PROMEGA). The Hsp70 5'UTR-luciferase or the FMDV-IRES-luciferase were cloned in the EcoR I site. All the constructs were sequence-checked.

Cell Culture Conditions

HepG2 and WI-38 cell lines were maintained in BME supplemented with 10% fetal bovine serum, 1% penicillin-streptomycin-glutamine. For HepG2 cells, medium was supplemented with 1% non essential amino acids, 1% sodium. Hep3B and HEK293 were maintained in MEM (Gibco Life Technologies, Inc) supplemented with 10% fetal bovine serum (HyClone) and 1% penicillin-streptomycin-glutamine. Cells were maintained at 37° C. in humidified air containing 5% $CO_2$.

Transient Transfections

HepG2, Hep3B, 293 and WI-38 cells were transiently transfected with the indicated construct and the internal control pRL-TK vector for luciferase assay or pSVe-βGal vector for CAT assay, using the calcium phosphate co-precipitation method.

Quantification of Reporter Genes Activities

Reporter gene activities were quantify 48 hours after transfection. In heat-shock experiments, 48 h hours after transfection the cells were heat-shocked at 42° C. for 40 minutes and then maintained 4 hours at 37° C. before luciferase activities were measured.

Luciferase activities were quantified using the Dual Luciferase Assay (Promega). Values were normalised with the renilla luciferase activity expressed from pRL-TK. CAT activities were normalised with the β galactosidase activity expressed from pSVe-βGal.

CAT mRNA Quantification

The $^{33}P$ CAT probe was synthetized with linearized pTRI-CAT vector (CAT Direct™: CAT mRNA detection kit, Ambion) using MaxiScrip™: in vitro transcription kit (Ambion), according to the manufacturer's protocol.

Confluent transfected cells were washed with phosphate-buffered saline (PBS). Cells were lysed in TRIZOL (Gibco, Life Technologies, Inc). Total mRNA was extracted using a 24:1 v/v of chloroform/isoamyl alcohol. Total mRNA was pelleted with an equal volume of isopropanol. Pellet was washed with a cold 70% ethanol solution and then solubilized in lysis buffer of Direct Protect™ kit (Lysate Ribonuclease Protection Assay, Ambion).

CAT mRNAs were quantified by a lysate ribonuclease protection assay using Direct Protect™ kit (Ambion) according to the manufacturer's protocol.

Protected fragments were resolved in 5% poly-acrylamide gels containing 8M urea and radioactivity was quantified using a Phosphorimager (STORM, Molecular Dynamics).

Example 1

Effect of the 5'UTR of the Human HSP70 mRNA on the Expression of a Luciferase Reporter Driven by the HSP70 Promoter (FIG. 1)

The human HSP70 promoter was cloned upstream of the coding sequence of the firefly luciferase gene in the absence or presence of the 5' UTR (plasmids A and B respectively). HepG2 cells were transfected with these two chimeric constructs and the levels of luciferase were compared either in normal conditions or after a 30 min heat-shock at 42° C. The presence of the 5'UTR of the human HSP70 mRNA by itself strongly increased the level of expression of the luciferase. Under both conditions (normal and heat-shock) a similar 9-fold stimulation was observed in the presence of the 5'UTR demonstrating that this increase in the luciferase expression is inherent to this 5'UTR and independent of the stress. Therefore, it can be expected that the human Hsp70 5'UTR can be used to enhance the expression of a wide variety of genes in normal cellular conditions.

Example 2

Effect of the 5'UTR of the Human HSP70 mRNA on the Expression of Luciferase in Various Cell Lines (FIG. 2)

HSPs are ubiquitous proteins and the heat-shock response is a highly conserved mechanism. Therefore, a similar effect of the human Hsp70 5'UTR was expected in other cell lines. Three other human cell lines were transfected with the same constructs. Hep3B is a hepatic cell line very close to HepG2. The two other cell lines tested, WI-38 and HEK293, are from different origins. WI-38 is a fibroblast-like cell line derived from embryonic lung tissue and HEK293 is a transformed primary embryonal kidney cell line. As shown in FIG. 2, the 5'UTR of the human HSP70 mRNA increased the expression of the luciferase gene in the three cell lines tested. An ~9-fold stimulation was obtained in the presence of the 5'UTR in Hep3B cells comparable to the stimulation observed in HepG2. In WI-38 and HEK293 cells the effect of the 5'UTR was less (a ~5-fold stimulation) but still significant, showing that this 5'UTR effect is not cell type specific. Therefore, it can be expected that this sequence can be used in a broad spectrum of applications where genes are expressed in various cell.

Example 3

Effect of the Human HSP70 5'UTR on the Translational Efficiency of the Chloramphenicol-acetyl-transferase mRNA (FIG. 3)

A higher level of luciferase expression in the presence of the HSP70 5'UTR can be explained either by a higher level of luciferase mRNA (due to an increase either in transcription or in mRNA stability) or by a more efficient translation of the luciferase mRNA. In order to distinguish between these two possible mechanisms, the mRNA levels in the absence or in the presence of the HSP70 5'UTR (plasmid H and I, respectively) were measured in transfected HepG2 cells. In this experiment CAT gene was used as reporter and was driven by the SV40. As previously observed with the luciferase gene, the presence of the HSP70 5'UTR cloned upstream of the coding sequence of the CAT gene increased (~10-fold) the CAT activity. Moreover, this higher level of CAT was achieved without any significant change in the CAT mRNA level in the presence of the HSP70 5'UTR. This result shows that the HSP70 5'UTR increases the translational efficiency of the mRNA independently of the reporter gene or the promoter used. Therefore, it can be expected that this human Hsp70 5'UTR property of increasing translational efficiency can be obtained for a wide variety of genes and promoters and can thus be used for a broad range of applications.

Example 4

Effect of Human Hsp70 5'UTR on the Expression of the Luciferase in Presence of the SV40 3'UTR (FIG. 4)

The 3'UTR present downstream of the reporter coding sequence in commercially available plasmids is frequently the 3'UTR of the SV40 large T antigen. This viral 3'UTR is known to allow a high level of expression of the reporter in transfection experiments. In order to determine if the human HSP70 5'UTR can increase the expression of the luciferase with this heterologous SV40 3'UTR we generated two vectors containing the SV40 3'UTR in the presence or absence of the human HSP70 5'UTR (plasmid C and D respectively). As expected (FIG. 4) the SV40 large T antigen 3'UTR allowed a high level of expression of the luciferase gene in the three cell lines tested. A 5- to 10-fold higher level of luciferase was observed in presence of this viral 3'UTR in comparison to the levels of expression obtained with the human HSP70 3'UTR (FIGS. 1 and 2). Nevertheless, the presence of the human HSP70 5'UTR was still able to increase the level of the luciferase expression by a 2-fold factor in the three cell lines tested.

Example 5

The Effect on Translation is not a Common Property of all Stress Protein 5'UTR (FIG. 5)

In order to compare the effect of the HSP70 5'UTR with another stress protein 5'UTR, the human GRP78 5'UTR was used. The human GRP78 5'UTR has a similar length as the HSP70 5'UTR (221bp versus 215pb for HSP70), and both of them are equally G+C rich (63%). Using the MFOLD program (Zuker M. and Jacobson A. B. (1995) Nucleic Ac. Res. (23) 2791-2798) to calculate the stability of these two 5'UTRs, a similar high □G value was found (~–60 kCal/mol), suggesting that these two 5'UTRs form structures of comparably high stability. Therefore the GRP78 5'UTR was an interesting 5'UTR to compare to the HSP70 5'UTR. As shown in FIG. 5, this 5'UTR (plasmid G) does not modify the level of expression of the luciferase gene. This result shows that the effect obtained with the HSP70 5'UTR is not a common property of all stress protein 5'UTRs.

Example 6

The Hsp70 5'UTR does not Behave as an Internal Ribosomal Entry Site (IRES) (FIG. 6)

IRES stuctures are found in the 5'UTR region of picornaviral mRNAs as well as in few eukaryotic mRNAs (Sachs A. B. et al (1997) Cell (89) 831-838). These structures allow a cap-independent protein translation. The decisive experiment to reveal an IRES structure is the use of a dicistronic plasmid with the putative IRES cloned between two Open-Reading-Frames (ORFs) under the control of one unique promoter. When the sequence contains an IRES structure the second ORF is translated independently of the presence of an upstream first ORF. Such plasmids were obtained with either the Human Hsp70 5'UTR (plasmid J) or with a classical IRES structure (the Foot and Mouth Disease Virus IRES (FMDV-IRES)) (plasmid K) or without any sequence (plasmide L) between the first ORF and the luciferase gene (second ORF). As shown in FIG. 6, the FMDV-IRES is capable of initiating the translation of the luciferase in a dicistronic context. In contrast no luciferase activity is obtained either with the Human Hsp70 5'UTR or without any sequence upstream of the luciferase coding sequence. This result shows that the Human Hsp70 5'UTR does not contain an IRES structure.

Example 7

Effect of HSP70 Element on Expression of Ovalbumin Protein in vitro

To determine whether the translation-enhancing properties of the HSP70 5' UTR element would be advantageous in DNA vaccination, we constructed a series of expression plasmids for the model antigen chicken ovalbumin. The plasmids all incorporate a common backbone derived from the vector pCI (Promega, Southampton, UK). Key elements in this plasmid are the immediate early promoter from human cytomegalovirus, which drives expression of the inserted antigen, a SV40 polyadenylation and transcription terminator sequence and the ampicillin resistance gene.

A cDNA cassette encoding the entire coding region of the chicken ovalbumin gene (GenBank accession V00383) was inserted into the plasmid between the promoter and SV40 element, creating pOvaREP. A second variant was prepared (pOvaOLD), containing an ATG sequence upstream from the ovalbumin gene translation initiation codon. This alteration markedly suppresses translation efficiency in transcripts from pOvaOLD compared with pOvaREP. The 5'UTR element of HSP70 was cloned into both vectors, creating pHSPOvaREP and pHSPOvaOLD.

All four constructs were sequence validated before being transiently transfected into four different cell lines (HepG2, 293, HeLa and CHO cells) to evaluate expression levels. To allow correction for transfection efficiency, a fixed amount of a luciferase expression plasmid (pGL3-Control; Promega) was also included in each transfection. Culture supernatant was collected 48 hours (CHECK) after transfection, and assayed for luciferase activity and ovalbumin content by ELISA.

The ovalbumin production in each sample was normalised for transfection efficiency using the luciferase activities. Relative protein expression levels are represented as a ratio of levels seen with and without the HSP70 element (see Table 1 below). No meaningful results were obtained for the pOvaOLD and pHSPOvaOLD constructs as the levels of ovalbumin produced were beneath the detection limit of the assay. However, pHSPOvaREP produced significantly more ovalbumin than pOvaREP in all four cell lines. The effect of the HSP70 element was most marked in the 293 cell line.

TABLE 1

Effect of HSP70 element on ovalbumin production from pOva plasmids in vitro.

| Cell type | Ratio Ova expression pHSPOvaREP:pOvaREP |
|---|---|
| CHO | 1.5 |
| HeLa | 1.7 |
| HepG2 | 1.9 |
| 293 | 3.0 |

Data are the means of triplicate determinations.

Example 2

Immunisation of Mice with Ovalbumin Expression Plasmids Containing HSP70 5'UTR Element The four plasmids described in Example 1 were used to vaccinate female Balb/c mice by biolistic gene delivery (REF-PJV patents). Animals were divided into groups of 6 and given two shots of 0.5 ug of plasmid at day 0 and again at day 43. Serum samples were taken at day −1, day 21, day 42, day 57 and day 71. Specific anti-ovalbumin IgG titres were determined by ELISA.

All four plasmids induced a similar response to the priming dose, with no apparent differences between groups at the day 21 and day 42 time points. However, following the day 43 immunisation, significant differences emerged (Table 2). Inclusion of the HSP70 5'UTR element enhanced the immune response to both the poor-expressing pOvaOLD and the optimally-expressing pOvaREP. These data suggest that the HSP70 5'UTR element is useful in enhancing the efficacy of DNA vaccination.

TABLE 2

Anti-ovalbumin IgG titres in vaccinated mice

| Plasmid | Reciprocal titre |
|---|---|
| pOvaOLD | 1100 |
| pHSPOvaOLD | 1500 |
| pOvaREP | 7000 |
| pHSPOvaREP | 10000 |

Anti Ova antibody titres were determined at the half-maximal absorbance value. Bleeds were from 57 days post primary immunisation.

The present invention thus also provides a DNA molecule according to the invention for use in therapy, preferably in therapeutic or prophylactic vaccination, for example when administered by particle bombardment, most preferably for use in achieving an increased immune response.

The present invention further provides a method of therapeutic or prophylactic vaccination comprising administering an effective amount of a DNA molecule according to the invention. Preferably the DNA molecule is administered by particle bombardment, most preferably for use in achieving an increased immune response.

DEFINITIONS

For the avoidance of doubt, certain terms used herein are further defined below. Similar terms should be construed accordingly.

"Polypeptide"

This means any moiety having a plurality of amino-acids joined together by peptide bonds. It includes proteins and peptides.

"About"

When used in connection with a numerical value this term allows for a margin either side of the value. Preferably the margin is +/−10% of the figure. more preferably it is +/−5%

"Sequence Identity"

For the purposes of the present invention, sequence identity may be determined, for example, by using the ALIGN program (version 2.0). This calculates a global alignment of two sequences. (See Myers and Miller, (1989) CABIOS, 4, 11-17). Gap penalties: −16/−4. For information see http://www.infobiogen.fr/services/menuserv.html "Substantial Sequence Identity"

This term is used to include polynucleotide sequences having at least 50% sequence identity with a given polynucleotide sequence. Preferably the degree of sequence identity is at least 75%. Sequence identities of at least 90%, at least 95% or at least 99% are most preferred.

"Heat Shock"

This is an increase in temperature which is sufficient to induce the heat shock response. Classically for cells a shift from 37° C. to 42° C. for 30 minutes is used to induce a heat shock.

"Increased Efficiency of Translation"

This means that a greater degree of translation to provide active polypeptides is obtained from a given number of mRNA molecules than would otherwise be the case.

REMARKS

The foregoing description of the invention is merely illustrative thererof and it should therefore be appreciated that various variations and modifications can be made without departing from the spirit or scope of the invention as set forth in the accompanying claims.

Where preferred or optional features are described in connection with particular aspects of the present invention, they shall be deemed to apply mutatis mutandis to othe aspects of the invention unless the context indicates otherwise.

All documents cited herein are hereby incorporated by reference, as are any citations referred to in said documents.

---

The invention claimed is:

1. A DNA molecule that can be transcribed to provide an RNA molecule having an untranslated region that provides an increased efficiency of translation of a therapeutic polypeptide in vivo when operably linked to a region encoding said polypeptide; wherein said DNA molecule
   (i) does not encode a mammalian Hsp70
   (ii) does not comprise an hsp promoter; and
   (iii) comprises
      (a) the sequence:

5'ataacggctagcctgaggagctgctgcgacagtccactacctttttc gagagtgactcccgttgtcccaaggcttcccagagcgaacctgtgcggct gcaggcaccggcgcgtcgagtttccggcgtccggaaggaccgagctcttc tcgcggatccagtgttccgtttccagcccccaatctcagagccgagccga cagagagcagggaaccgc-3' (SEQ ID NO: 1), (b) the complement of the sequence given in (a), or
   (c) a sequence having sequence identity of at least 90% with a sequence as defined in (a) or (b) above.

* * * * *